(12) United States Patent
Klauck-Jacobs et al.

(10) Patent No.: US 6,894,200 B2
(45) Date of Patent: *May 17, 2005

(54) SYNTHESIS OF VICINAL DIFLUORO AROMATICS AND INTERMEDIATES THEREOF

(75) Inventors: Axel Klauck-Jacobs, Whitehall, PA (US); Kathryn Sue Hayes, Plymouth Meeting, PA (US); Reiner Taege, Heiligenhaus (DE); William Casteel, Emmaus, PA (US); Gauri Sankar Lal, Whitehall, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 142 days.

This patent is subject to a terminal disclaimer.

(21) Appl. No.: 10/357,897

(22) Filed: Feb. 3, 2003

(65) Prior Publication Data

US 2003/0149315 A1 Aug. 7, 2003

Related U.S. Application Data

(63) Continuation-in-part of application No. 10/197,969, filed on Jul. 17, 2002, now Pat. No. 6,515,191, which is a division of application No. 09/985,786, filed on Nov. 6, 2001, now Pat. No. 6,455,744, which is a continuation of application No. 09/767,636, filed on Jan. 23, 2001, now abandoned.

(51) Int. Cl.$^7$ .............................................. C07C 25/22
(52) U.S. Cl. ........................................ 570/143; 570/123
(58) Field of Search .................................. 570/123, 143

(56) References Cited

U.S. PATENT DOCUMENTS

| 6,455,744 B1 | 9/2002 | Lal et al. |
| 2003/0149315 A1 | 8/2003 | Jacobs et al. |

FOREIGN PATENT DOCUMENTS

| DE | 197 43 109 A1 | 4/1999 |
| JP | 2001 354600 A | 12/2001 |

*Primary Examiner*—Golam M M Shameem
(74) *Attorney, Agent, or Firm*—Geoffrey L. Chase

(57) ABSTRACT

A method of preparing vicinal difluoro aromatic compounds in high yield from hydroxy aromatic compounds using various bases and a method of preparing intermediates thereof. A method for making a vicinal difluoro halogenated aromatic compound including providing a tetrafluoro derivative of a halogen substituted aromatic compound, wherein the tetrafluoro derivative has two fluorine atoms on each of two adjacent carbons and at least one additional halogen substituent; reacting the tetrafluoro derivative with a reducing agent in presence of a base for a reaction time sufficient to form the vicinal difluoro halogenated aromatic compound containing two vicinal fluorine substituents and the at least one additional halogen substituent, wherein the reducing agent is used in a reducing agent effective amount sufficient to retain the at least one additional halogen substituent.

11 Claims, No Drawings

SYNTHESIS OF VICINAL DIFLUORO AROMATICS AND INTERMEDIATES THEREOF

CROSS REFERENCE TO RELATED APPLICATIONS

This application is a continuation-in-part of application Ser. No. 10/197,969, filed on Jul. 17, 2002, now U.S. Pat. No. 6,515,191, which is a division of application Ser. No. 09/985,786, filed on Nov. 6, 2001, now U.S. Pat. No. 6,455,744, which is a continuation-in-part of application Ser. No. 09/767,636, filed on Jan. 23, 2001, now abandoned.

BACKGROUND OF THE INVENTION

This invention relates to a process for making vicinal difluoro aromatics using a reducing agent in the presence of various bases. Also, conditions were found to allow making halogen-substituted 1,2-difluoronaphthalenes in high yields. Vicinal difluoro aromatics, e.g., halogen-substituted 1,2-difluoronaphthalenes may be used as intermediates for liquid crystal materials.

Aromatic compounds, especially naphthalene derivatives bearing fluorine atoms on adjacent (i.e., vicinal) carbons, have been found to be useful as liquid crystal materials or their intermediates. They are typically made by a multi-step process, starting from the aromatic amine via a fluoro-dediazoniation process (N. Yoneda and T. Fukuhara, Tetrahedron, vol. 52, No. 1 (1996), pages 23–36). No simple methods are known for producing vicinal difluoro aromatic compounds. Methods for defluorinating highly fluorinated compounds are known, but none of the methods has been shown to produce vicinal difluoro compounds in high yield. For example, C. Hu et al., Journal of Fluorine Chemistry, vol. 48 (1990), pp. 29–35 disclose a method of synthesizing perfluoroaromatics, such as tetradecafluorobicyclo(4.4.0)dec-1(2),6(7)-diene and perfluorotetralin, by defluorination of hexadecafluorobicyclo(4.4.0)dec-1(6)-ene in an aprotic solvent using activated zinc powder as a reagent. The extent of defluorination depended on the polarity of the aprotic solvent used.

J. Burdon and I. W. Parsons, Journal of Fluorine Chemistry, vol. 13 (1979), pages 159–162, disclose the formation of 2,5-difluorothiophen by pyrolysis of 2,2,5,5-tetrafluoro-3-thiolen over sodium fluoride.

Sergey S. Laev and Vitalii D. Shteingarts, Journal of Fluorine Chemistry, vol. 96 (1999) pp. 175–185, disclose the reductive dehalogenation of polyfluoroarenes by zinc in ammonium hydroxide. In the reaction, hydrogen atoms replace fluorine atoms in the polyfluoroarenes.

JP 2001-10995A to Ogawa et al. describes a four-step process for synthesis of vicinal difluoro aromatic compounds involving fluorination of a hydroxy aromatic compound to form a tetrafluoro intermediate in two steps followed by hydrogenation and defluorination under basic conditions. This reference also discloses reduction of a difluoroketone intermediate with aluminum isopropoxide and then base-catalyzed dehydrohalogenation to form a difluoro aromatic compound. A third method involves reaction of the difluoroketone with lithium aluminum hydride to form a fluoroepoxide, addition of HF, and elimination of water to give a vicinal difluoro aromatic compound. The best overall yield shown is <50%.

JP2001-354600 to Kusunoki et al. discloses a process for making 6-bromo-1,2-difluoronaphthalene from 6-bromo-2-hydroxynaphthalene. The first step involves reaction of the substrate with SELECTFLUOR® fluorinating reagent to form 6-bromo-1,1-difluoro-1H-naphthalene-2-one in 95% yield. In the second step, the difluoro intermediate is fluorinated with DAST to form 6-bromo-1,1,2,2-tetrafluoro-1,2-dihydronaphthalene in 72% yield. Finally, the tetrafluoro intermediate is defluorinated using 5% Rh/C to give 6-bromo-1,2-difluoronaphthalene in 69% yield. The overall yield is only 47%.

JP2002-201145 to Yokooji et al. discloses a process for fluorinating hydroxynaphthalenes with 5% fluorine in nitrogen. Fluorination of 6-bromo-2-hydroxynaphthalene gives only 45% 6-bromo-1-fluoro-2-hydroxynaphthalene and 10% 6-bromo-1,1-difluoro-1H-naphthalene-2-one.

The parent U.S. Pat. No. 6,455,744 B1 to Lal et al. discloses a three-step process for making 1,2-difluoronaphthalenes from 2-hydroxynaphthalenes. Example 11 of the patent shows that after the treatment of 6-bromo-1,1,2,2-tetrafluoro-1,2-dihydronaphthalene with zinc in THF and NH$_4$OH, debromination is observed and 1,2-difluoronaphthalene is produced; i.e., bromine is removed from 6-bromo-1,1,2,2-tetrafluoro-1,2-dihydronaphthalene as well as two fluorines.

Despite the foregoing developments, it is desired to provide additional processes for making vicinal difluoro aromatics, e.g., halogenated vicinal difluoro aromatic compounds in high yields.

All references cited herein are incorporated herein by reference in their entireties.

BRIEF SUMMARY OF THE INVENTION

This invention is directed to a method of preparing vicinal difluoro aromatic compounds in high yield from hydroxy aromatic compounds using a reducing agent in the presence of various bases and to preparing intermediates thereof. The method for making an aromatic compound having two vicinal fluorine atoms comprises mixing a tetrafluoro derivative of an aromatic compound with a reducing agent in a presence of a base for a time needed to form an aromatic compound containing two vicinal fluorine atoms, said tetrafluoro aromatic compound having two fluorine atoms on each of two adjacent carbons on the ring. The hydroxy aromatic compound can be a mono-, bi- or tricyclic aromatic in which the rings are separate or fused. One or more of the rings can contain heteroatoms, such as oxygen, nitrogen, or sulfur, and can contain substitutions, in addition to the hydroxy substitution. Substitutions on one or more of the rings can include a halogen atom, a $C_1$ to $C_{20}$ alkyl, a $C_5$–$C_{10}$ cycloalkyl, a $C_6$ to $C_{12}$ aryl, an amino, a nitro, a $C_1$ to $C_{10}$ alkyl ether or thioether, a $C_1$ to $C_{10}$ alkyl ester, a $CF_3$, a R'SO$_2$O,

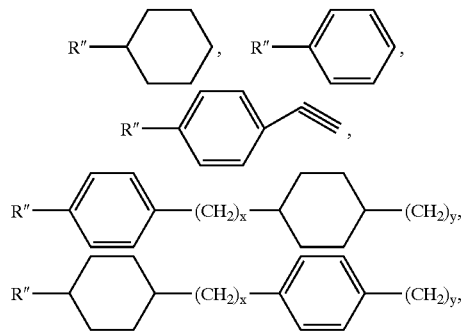

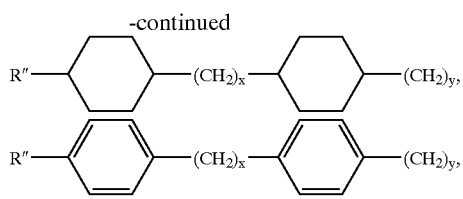

where R' is $CF_3$, a $C_1$ to $C_{20}$ alkyl, a substituted or unsubstituted $C_5$ to $C_{10}$ cycloalkyl, or a substituted or unsubstituted $C_6$ to $C_{12}$ aryl, in which the substitution on the cycloalkyl or aryl can be a $C_1$ to $C_{20}$ alkyl or a $C_5$ to $C_8$ cycloalkyl; R" is a $C_1$–$C_{10}$ saturated or unsaturated alkyl; x is an integer from 0 to 10, and y is an integer from 0 to 10.

Also, this invention is directed to a method for making a vicinal difluoro halogenated aromatic compound and intermediates thereof, said method comprising:

providing a tetrafluoro derivative of a halogen substituted aromatic compound, wherein the tetrafluoro derivative has two fluorine atoms on each of two adjacent carbons and at least one additional halogen substituent; and reacting the tetrafluoro derivative with a reducing agent in presence of a base for a reaction time sufficient to form the vicinal difluoro halogenated aromatic compound containing two vicinal fluorine substituents and the at least one additional halogen substituent, wherein the reducing agent is used in a reducing agent effective amount sufficient to retain the at least one additional halogen substituent.

This method of preparing vicinal difluoro aromatic compounds and particularly halogenated vicinal difluoro aromatic compounds has the following advantages over known methods:

- the difluoroketone and tetrafluoro intermediates do not need to be purified prior to subsequent reaction,
- the product is produced in high selectivity,
- the overall yield is 70% or more for vicinal difluoro aromatic compounds and 60% or more for halogenated vicinal difluoro aromatic compounds, and
- the product easily can be easily separated and purified by known methods.

DETAILED DESCRIPTION OF THE INVENTION

This invention is directed to a method of preparing vicinal difluoro aromatic compounds in high yield from hydroxy aromatic compounds using a reducing agent in the presence of various bases and to preparing intermediates thereof. The inventors have discovered that various bases such as ammonium hydroxide, hydroxylamine, hydrazine, and substitutes and hydrates thereof can be used to prepare vicinal difluoro aromatic compounds. The non-limiting examples of a substituted ammonium hydroxide and hydrates thereof are tetramethylammonium hydroxide, tetramethylammonium hydroxide pentahydrate, ethyl ammonium hydroxide, and benzyltrimethyl ammonium hydroxide. The non-limiting examples of a substituted hydrazine are methylhydrazine and phenylhydrazine. In certain embodiments of the invention, vicinal difluoro aromatic compounds are prepared in a reaction conducted in a broad range of temperatures including −25 to 90° C.

In addition, this invention is directed to a method of preparing halogenated vicinal difluoro aromatic compounds in high yield from hydroxy aromatic compounds and to preparing intermediates thereof. One of the goals of the present invention is to develop a method to selectively dehalogenate tetrafluoro derivatives of halogenated vicinal aromatic compounds, wherein loss of halogen is avoided or minimized. Reaction conditions have been identified that minimize loss of halogens, such as bromine, during deflu-orination. Accordingly, the process of the invention provides the desired halogenated vicinal difluoro aromatic compounds in yields greater than 69%, and more preferred in yields greater than 80%. Surprisingly, the inventors have found that the inventive reaction could be successfully conducted with much less reducing agent than used previously (see Example 11 of U.S. Pat. No. 6,455,744 B1 to Lal et al.).

The process of the present invention can be described by the following reaction steps:

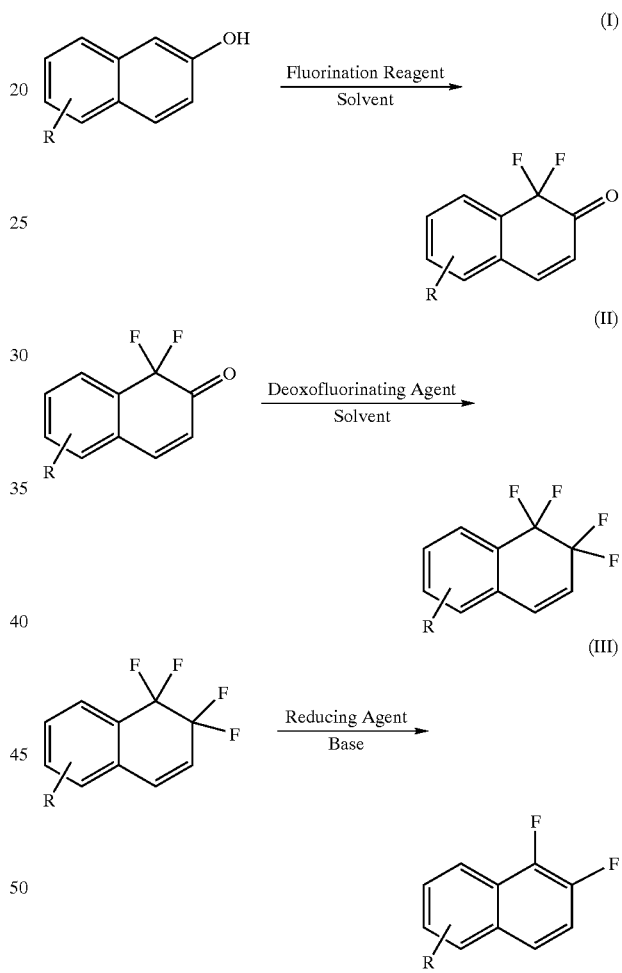

where R is a hydrogen atom, a halogen atom (Cl, Br, I, F), $R'SO_2O$, $CF_3$, a fused aryl, a C1–C20 alkyl, amino, nitro, a C1 to C10 ether or thioether, a C1 to C10 ester, a heteroaryl, wherein the heteroatom can be O, N, S,

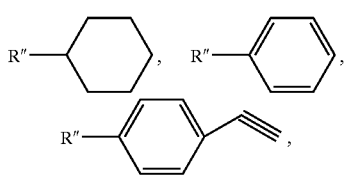

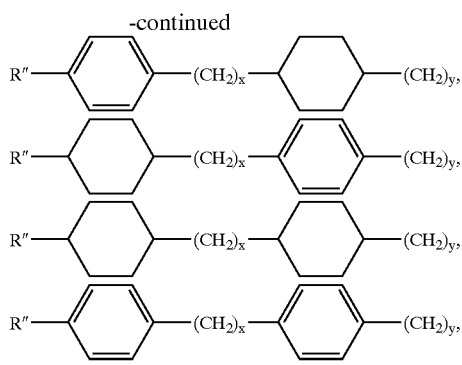

or R forms an aryl, R' is $CF_3$, a $C_1$ to $C_{20}$ alkyl, a substituted or unsubstituted $C_5$ to $C_{10}$ cycloalkyl, or a substituted or unsubstituted $C_6$ to $C_{12}$ aryl, in which the substitution on the cycloalkyl or aryl can be a $C_1$ to $C_{20}$ alkyl or a $C_5$ to $C_8$ cycloalkyl; R" is a $C_1$–$C_{10}$ saturated or unsaturated alkyl; x is an integer from 0 to 10, and y is an integer from 0 to 10. The preferred R group is trans-4-propylcyclohexyl.

In the method of this invention, vicinal difluoro aromatic compounds can be prepared in three steps from hydroxy aromatic compounds by electrophilic fluorination using a fluorination reagent such as SELECTFLUOR® reagent (1-chloromethyl-4-fluoro-1,4-diazabicyclo(2.2.2)octane bis-tetrafluoroborate) to form a difluoroketone intermediate. The difluoro ketone undergoes nucleophilic fluorination by reaction with a deoxofluorinating reagent such as DEOXO-FLUOR® reagent (bis(2-methoxyethyl)-aminosulfur trifluoride) to give a tetrafluoro intermediate species. The tetrafluoro intermediate is defluorinated by a metallic reducing agent in the presence of a base to provide the desired vicinal difluoro aromatic compound in high yield. Various bases such as ammonium hydroxide, hydroxylamine, hydrazine, and substitutes and hydrates thereof can be used. The non-limiting examples of a substituted ammonium hydroxide and hydrates thereof are tetramethylammonium hydroxide, tetramethylammonium hydroxide pentahydrate, ethyl ammonium hydroxide, and benzyltrimethyl ammonium hydroxide. The non-limiting examples of a substituted hydrazine are methylhydrazine and phenylhydrazine.

In the first step, a hydroxy aromatic compound (e.g., β-naphthol or substituted naphthol) is reacted with an electrophilic fluorinating agent such as SELECTFLUOR® reagent, to generate a difluoroketone intermediate. This reaction can be conducted in various solvents including nitriles such as acetonitrile ($CH_3CN$), formamides such as dimethylformamide (DMF), $CH_3NO_2$, carboxylic acids such as acetic acid, water, and an alcohol such as methanol, ethanol, and propanol.

The reaction can be carried out at temperatures ranging from 0° C. to the boiling point of the solvent.

The fluorinating agent can be added to a solution or suspension of the hydroxy aromatic compound in one or more portions, or dropwise as a solution or a suspension. Alternatively, the hydroxy aromatic compound solution or suspension can be added to a solution or suspension of fluorinating agent.

In the second step, the carbonyl oxygen of the difluoroketone is replaced by two fluorine atoms using a deoxofluorinating agent such as DEOXO-FLUOR® reagent. The reaction is carried out by reacting the difluoroketone with the deoxofluorinating agent in an organic solvent in an anhydrous atmosphere. Solvents include alkanes such as hexane, heptane, etc.; aromatic hydrocarbons such as toluene, xylenes, etc.; haloalkanes such as methylene chloride, chloroform, etc.; ethers, such as diethyl ether, THF, etc.; and any other solvent that will not react with the fluorinating reagent.

The reaction temperature can range from 0° C. to 90° C. In carrying out the reaction, the difluoroketone can be mixed with the entire charge of the fluorinating reagent or the reagent can be added dropwise to a solution of the difluoroketone. Lewis acid catalysts such as boron trifluoride etherate ($BF_3Et_2O$) or HF can be used to accelerate the reaction. The product obtained is usually a mixture of the desired 1,1,2,2-tetrafluoro compound and the corresponding 1,1,2,4-tetrafluoro isomer. We have found that both the yield and the isomer ratio are highly dependent on the solvent used. Toluene is unexpectedly superior to other organic solvents in producing a high yield of the desired isomer. For example, when THF was used as solvent at 60° C., a 65% yield of 1,1,2,2-tetrafluoro-6-(trans-4-propylcyclohexyl)-1,2-dihydronaphthalene was obtained (1,1,2,2-tetrafluoro/1,1,2,4-tetrafluoro=51/49), while when toluene was used as solvent at the same temperature, an 85% yield was obtained (1,1,2,2-tetrafluoro/1,1,2,4-tetrafluoro=90/10) under the same reaction conditions.

In the third step of the process, the mixture of tetrafluoro isomers is reductively defluorinated using a reducing agent in the presence of a base. Both tetrafluoro isomers react to form the same vicinal difluoro aromatic product.

The reducing agent in this method can be metallic zinc or other known reducing agents, such as copper, magnesium, or mixtures thereof. The metals typically are used in powder form, but other forms should also be effective. Reducing agents that do not react rapidly with water are preferred. At least one molar equivalent of the reducing agent, based on the amount of starting compound, is needed.

The process of reductive defluorination is preferably carried out in the presence of a base to provide the desired vicinal difluoro aromatic compound in high yield. Bases include inorganic bases such as sodium hydroxide, potassium hydroxide, and ammonium hydroxide and substitutes and hydrates thereof, wherein ammonium hydroxide is preferred. Organic bases include hydroxylamine, hydrazine and substitutes and hydrates thereof. The non-limiting examples of a substituted ammonium hydroxide and hydrates thereof are tetramethylammonium hydroxide, tetramethylammonium hydroxide pentahydrate, ethyl ammonium hydroxide, and benzyltrimethyl ammonium hydroxide, wherein tetramethylammonium hydroxide is preferred. The non-limiting examples of a substituted hydrazine are methylhydrazine and phenylhydrazine.

In certain embodiments of the present invention, the base is used in the presence of an inorganic or an organic co-solvent including ethers, nitrites, alcohols, and amides, preferably tetrahydrofuran (THF), methyl tert-butyl ether, acetonitrile, ethanol, or dimethylformamide, and most preferably THF. The base is buffered to a pH <14 and preferably to a pH <11 with an ammonium salt; preferably ammonium chloride. Maintaining a pH below 14, minimizes the production of unwanted by-products. For example, when the reaction medium is too basic (i.e., a pH of 14), 1,1,2,2-tetrafluoro dihydronaphthalene is converted to a 1,2,4-trifluoronaphthalene compound as shown in the reaction below:

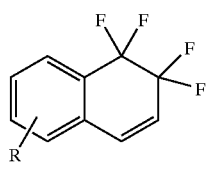 Base → 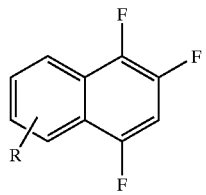

The rate of this reaction has been found to be pH-dependent, and consequently the selectivity to this impurity is significantly reduced as the pH is reduced below 14, especially below 11.

Typically 3.2 ml of ammonium hydroxide and 1.6 ml of organic solvent per mmol of starting compound are appropriate for the reaction.

The reaction can be carried out at temperatures ranging from about −25 to about 90° C., preferably from 0° C. to the boiling point of the solvent, and more preferably from about 25 to about 45° C. The reaction can be run in air, under vacuum or under an inert gas, such as nitrogen.

The reaction can be monitored by methods known in the art to determine completion. For example GC or GC/MS (gas chromatography/mass spectrometry) can be used to determine when the reaction is complete. Reaction times typically range from 2–48 hours.

The vicinal difluoro aromatic product can be isolated from the reaction mixture by methods known in the art. For example, the product can be isolated by filtering the reducing metal, extracting the aqueous layer into an immiscible organic solvent, evaporating the solvent, and purifying the product using chromatography, distillation, sublimation, and/or recrystallization.

The yields obtained from reactions (1) and (2) are highly dependent on the solvents employed for these steps. Polar aprotic solvents are desirable for the electrophilic fluorination in step (1) and dimethylformamide (DMF) is particularly preferred because it unexpectedly resulted in yields of greater than 95% difluoroketone product.

Reaction step (2) can be conducted in various solvents including aliphatic and aromatic hydrocarbons, halocarbons, ethers, etc.; however, toluene unexpectedly gives much higher yields of the tetrafluoro product compared to other organic solvents. Step (3) involves reacting the tetrafluoro compound with a reducing agent, such as metallic zinc, copper, magnesium, or a mixture thereof, in the presence of a base to form the vicinal difluoro aromatic compound in high yields (e.g., 90% or more). The base used in this reaction is preferably ammonium hydroxide, hydroxylamine, hydrazine, or a substituted ammonium hydroxide, wherein the substituted ammonium hydroxide is a member selected from the group consisting of tetramethylammonium hydroxide, ethyl ammonium hydroxide, and benzyltrimethyl ammonium hydroxide.

In certain embodiments of the present invention, the process for making halogen-substituted 1,2-difluoronaphthalenes is performed in three steps as shown below:

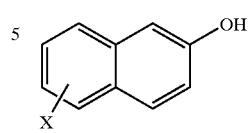 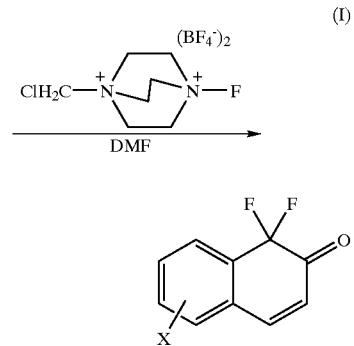 (I)

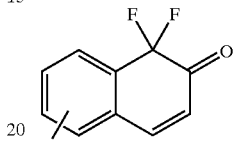 $\xrightarrow{(MeOCH_2CH_2)_2NSF_3 \text{ or } SF_4/HF}$ (II)

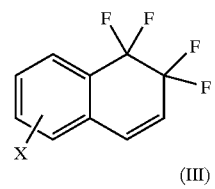 (III)

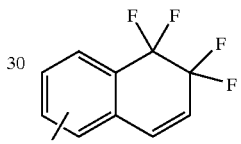 $\xrightarrow{Zn, NH_4OH/NH_4Cl \text{ or } Zn, R'''_4NOH}$

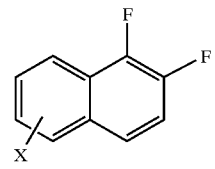

where X is Br, Cl, I or F; R''' is H, $C_1$ to $C_{20}$ alkyl, aryl, benzyl, or OH; and Me is methyl. In certain embodiments of the present invention, all four R''' substituent groups in R'''$_4$NOH are the same or a combination of different substituent groups named above.

The halogenated hydroxy aromatic compound can be a mono-, bi- or tricyclic aromatic in which the rings are separate or fused. One or more of the rings can contain heteroatoms, such as oxygen, nitrogen, or sulfur, and can contain substituents, in addition to the hydroxy and halogen substituents. Substitutions (R) on one or more of the rings can include, e.g., a halogen atom, a $C_1$ to $C_{20}$ alkyl, a $C_5$–$C_{10}$ cycloalkyl, a $C_6$ to $C_{12}$ aryl, an amino, a nitro, a $C_1$ to $C_{10}$ alkyl ether or thioether, a $C_1$ to $C_{10}$ alkyl ester, $CF_3$, R'$SO_2O$,

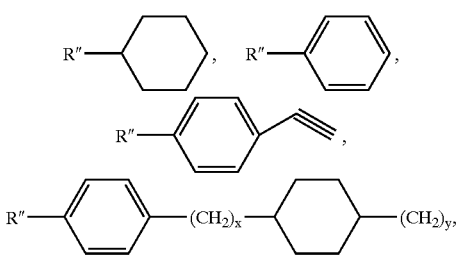

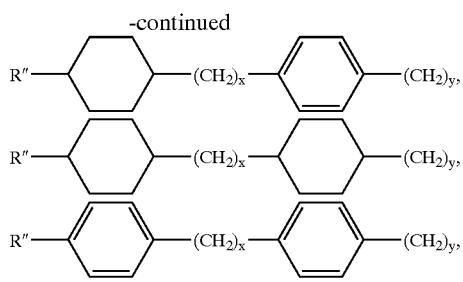

or R forms an aryl. R' is CF$_3$, a C$_1$ to C$_{20}$ alkyl, a substituted or unsubstituted C$_5$ to C$_{10}$ cycloalkyl, or a substituted or unsubstituted C$_6$ to C$_{12}$ aryl, in which the substitution on the cycloalkyl or aryl can be a C$_1$ to C$_{20}$ alkyl or a C$_5$ to C$_8$ cycloalkyl; R" is a C$_1$–C$_{10}$ saturated or unsaturated alkyl; x is an integer from 0 to 10, and y is an integer from 0 to 10. The preferred R group is trans-4-propylcyclohexyl.

Non limiting examples of such substituted halogenated vicinal difluoro aromatic compounds are shown below:

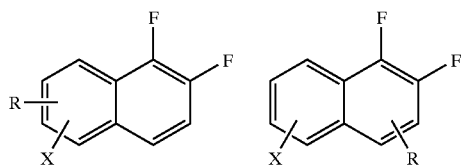

In the method of this invention, halogenated vicinal difluoro aromatic compounds can be prepared in three steps from halogenated hydroxy aromatic compounds by electrophilic fluorination using a fluorination reagent including SELECTFLUOR® reagent (1-chloromethyl-4-fluoro-1,4-diazabicyclo(2.2.2)-octane bis(tetrafluoroborate)) (available from Air Products and Chemicals Inc., Allentown, Pa.) to form a difluoroketone intermediate. The difluoroketone undergoes nucleophilic fluorination by reaction with a deoxofluorinating reagent including DEOXO-FLUOR® reagent (bis(2-methoxyethyl)-aminosulfur trifluoride) (available from Air Products and Chemicals Inc., Allentown, Pa.) or SF$_4$ and HF to give a tetrafluoro intermediate species. Next, the tetrafluoro intermediate is defluorinated by a reducing agent other then hydrogen in the presence of a base to provide the desired vicinal difluoro aromatic compound in high yield.

Bases include inorganic bases such as sodium hydroxide, potassium hydroxide, and ammonium hydroxide and substitutes and hydrates thereof, wherein ammonium hydroxide is preferred. Organic bases include hydroxylamine, hydrazine and substitutes and hydrates thereof. The non-limiting examples of a substituted ammonium hydroxide and hydrates thereof are tetramethylammonium hydroxide, tetramethylammonium hydroxide pentahydrate, ethyl ammonium hydroxide, and benzyltrimethyl ammonium hydroxide, wherein tetramethylammonium hydroxide is preferred. The non-limiting examples of a substituted hydrazine are methylhydrazine, and phenylhydrazine.

In certain embodiments of the present invention, the base is used in the presence of an inorganic or an organic co-solvent, preferably tetrahydrofuran (THF), methyl tert-butyl ether, acetonitrile, ethanol, or dimethylformamide, and most preferably THF.

In the first step, a halogenated hydroxy aromatic compound (e.g., 6-bromo-2-naphthol) is reacted with an electrophilic fluorinating agent, preferably SELECTFLUOR® reagent, to generate a difluoroketone intermediate. This reaction can be conducted in various solvents including nitriles such as acetonitrile (CH$_3$CN), formamides such as dimethylformamide (DMF), CH$_3$NO$_2$, carboxylic acids such as acetic acid, water, and an alcohol such as methanol, ethanol, and propanol. The reaction can be carried out at temperatures ranging from about 0° C. to the boiling point of the solvent, preferably from about 0° C. to about 30° C.

The fluorinating agent can be added to a solution or suspension of the hydroxy aromatic compound in one or more portions, or dropwise as a solution or suspension. Alternatively, the hydroxy aromatic compound solution or suspension can be added to a solution or suspension of fluorinating agent.

In the second step, the carbonyl oxygen of the difluoroketone is replaced by two fluorine atoms using a deoxofluorinating agent, preferably a nucleophilic deoxofluorinating reagent, more preferably DEOXO-FLUOR® reagent. In certain embodiments of the present invention, the deoxofluorinating agent is a mixture of SF$_4$ and HF.

The reaction is carried out by reacting the difluoroketone with the deoxofluorinating agent in a solvent in an anhydrous atmosphere. Solvents include organic solvents including alkanes such as hexane, heptane, etc.; aromatic hydrocarbons such as toluene, xylenes, etc.; haloalkanes such as methylene chloride, chloroform, etc.; ethers, such as diethyl ether, THF, inorganic solvents such as HF and any other solvent that will not react with the fluorinating reagent.

The reaction temperature can range from about –50° C. to about 90° C., preferably from about 0° C. to about 70° C. In carrying out the reaction, the difluoroketone can be mixed with the entire charge of the fluorinating reagent or the reagent can be added dropwise to a solution of the difluoroketone. Lewis acid catalysts such as boron trifluoride etherate (BF$_3$.Et2O) or HF can be used to accelerate the reaction. The product obtained is usually a mixture of the desired 1,1,2,2-tetrafluoro compound and the corresponding 1,1,2,4-tetrafluoro isomer. The inventors have found that both the yield and the isomer ratio are highly dependent on the solvent used. Toluene is unexpectedly superior to other organic solvents in producing a high yield of the desired isomer. In addition, the inventors have discovered that for halogenated difluoroketone compounds, SF$_4$ can be used as deoxofluorinating agent with HF as solvent while SF$_4$ did not work with other difluoroketone compounds.

In the third step of the process, the mixture of tetrafluoro isomers is reductively defluorinated using a reducing agent in the presence of a base as defined above. Both tetrafluoro isomers react to form the same vicinal difluoro aromatic product. The reducing agent in this step can be metallic zinc, copper, magnesium, or mixtures of these metals with each other or with other known reducing agents excluding hydrogen. The metals typically are used in a powder form, but other forms should also be effective. Reducing agents that do not react rapidly with water are preferred. Surprisingly, the inventors discovered that a smaller amount of the reducing agent is needed for converting tetrafluoro halogenated aromatic compounds than for converting other tetrafluoro aromatic compounds.

At least one molar equivalent of the reducing agent, based on the amount of starting compound, is needed. Preferably, the molar equivalent of the reducing agent is 1 to less than 8 times the molar amount of tetrafluoro isomers, more preferably 1.5–3 times, and even more preferably less than 2.5 times the molar amount of tetrafluoro isomers.

In certain embodiments of the invention, the process of reductive defluorination is preferably carried out in buffered ammonium hydroxide with an organic co-solvent, such as THF. The organic co-solvent can be used to make a solution of the tetrafluoro aromatic compound. Other co-solvents that can be used include but are not limited to ethers such as methyl tert-butyl ether; nitriles such as acetonitrile; alcohols such as ethanol; and amides such as DMF. The ammonium hydroxide is buffered to a pH<14 and preferably <11 with an ammonium salt; preferably ammonium chloride. Maintaining a pH below 14 minimizes the production of unwanted byproducts. For example, when the reaction medium is too basic (i.e., a pH of 14), 1,1,2,2-tetrafluoro dihydronaphthalene is converted to a 1,2,4-trifluoronaphthalene. The rate of this reaction has been found to be pH-dependent, and consequently the selectivity to this impurity is significantly reduced as the pH is reduced below 14, especially below 11.

Unexpectedly, the inventors found that the reaction can be carried out at temperatures ranging from about −25° C. to about 90° C., preferably from about 0° C. to about 50° C., and more preferably from about 0° C. to about 25° C. Preferably, the reagents are cooled to 0° C. prior to reacting and allowed to warm up to room temperature during the reaction process. The reaction can be run in air, in vacuum or in an inert gas atmosphere, preferably the inert gas includes nitrogen.

The reaction can be monitored by methods known in the art to determine completion. For example, GC or GC/MS (gas chromatography/mass spectrometry) can be used to determine when the reaction is complete. The vicinal difluoro aromatic product can be isolated from the reaction mixture by methods known in the art. For example, the product can be isolated by filtering the reducing agent, extracting the aqueous layer into an immiscible organic solvent, evaporating the solvent, and purifying the product using chromatography, distillation, sublimation, and/or recrystallization.

The invention will be illustrated in more detail with reference to the following Examples, but it should be understood that the present invention is not deemed to be limited thereto.

EXAMPLES

Example 1

Synthesis of 1,1-difluoro-(trans-4-propylcyclohexyl)-1H-naphthalene-2-one Using DMF Solvent A suspension of 6-(trans-4-propylcyclohexyl) naphthalene-2-ol (30 g, 111.9 mmol) in DMF (180 ml) was treated with SELECTFLUOR® reagent (79.9 g, 224.4 mmol) in 5 equal portions at 15 minute intervals. The mixture was stirred for a further 4 hours (h) at room temperature (RT). On completion, the reaction mixture was washed with water (2×100 ml) and NaHCO$_3$ (100 ml), dried (MgSO$_4$), filtered, and evaporated in vacuo. After purification by column chromatography on silica gel (ethyl acetate/hexanes 1/9), the product (33.6 g, 98%) was obtained. Use of DMF unexpectedly resulted in a substantially higher yield of product compared to use of CH$_3$CN in Example 2.

Example 2

Synthesis of 1,1-difluoro-(trans-4-propylcyclohexyl)-1H-naphthalene-2-one Using Acetonitrile Solvent A suspension of 6-(trans-4-propylcyclohexyl) naphthalene-2-ol (30 g, 111.9 mmol) in CH$_3$CN (225 ml) was treated with SELECTFLUOR® reagent (79.9 g, 224.4 mmol) in 5 equal portions at 15 min intervals. The mixture was stirred for a further 4 h at RT. On completion, the reaction mixture was extracted with 100 ml of toluene, washed with water (2×100 ml) and saturated NaHCO$_3$ (100 ml), dried (MgSO$_4$), filtered, and evaporated in vacuo. The residue was chromatographed on silica gel (ethyl acetate/hexanes 1/9) to obtain the product (25.37 g, 74%). MS: m/e=304 (M$^+$).

Example 3

Synthesis of 1,1,2,2-tetrafluoro-6-(trans-4-propylcyclohexyl)-1,2-dihydronaphthalene Using Toluene Solvent A solution of 1,1-difluoro-(trans-4-propylcyclohexyl)-1H-naphthalene-2-one (2.0 g, 6.6 mmol) in toluene (5 ml) was heated to 60° C. in a TEFLON tube under N$_2$. To this solution was added the DEOXO-FLUOR® reagent dropwise (2.48 g, 2.1 ml, 11.22 mmol). The mixture was heated for a further 5 h. On cooling to 0° C., the solution was treated with 0.5 ml of methanol (MeOH) and saturated NaHCO$_3$. After CO$_2$ evolution ceased the solution was diluted with 20 ml toluene and the organic layer was separated, dried (MgSO$_4$), filtered, and evaporated in vacuo. The residue was purified by chromatography on silica gel (hexanes as solvent) to obtain the pure product (1.82 g, 85% yield as a 90/10 mixture of the title product and the 1,1,2,4-tetrafluoro isomer). MS: m/e 326 (M$^+$).

Example 4

Synthesis of 1,1,2,2-tetrafluoro-6-(trans-4-propylcyclohexyl)-1,2-dihydronaphthalene Using THF Solvent A solution of 1,1-difluoro-(trans-4-propylcyclohexyl)-1H-naphthalene-2-one (2.0 g, 6.6 mmol) and DEOXO-FLUOR® reagent (2.48 g, 2.1 ml, 11.22 mmol) in THF (4 mL) was heated for 3 h at 60° C. in a TEFLON tube under N$_2$. On cooling to 0° C., the solution was treated with MeOH (0.5 ml) and saturated NaHCO$_3$. After CO$_2$ evolution ceased, the solution was diluted with 20 ml EtOAc and the organic layer was separated, dried (MgSO$_4$), filtered, and evaporated in vacuo. The residue was purified by chromatography on silica gel (hexanes as solvent) to obtain the pure product (1.39 g, 65% yield as a 51/49 mixture of the title product and the 1,1,2,4-tetrafluoro isomer). MS: m/e 326 (M$^+$).

Example 5

Synthesis of 1,1-difluoro-6-(trans-4-propylcyclohexyl)-1,2-dihydronaphthalene-2-one A solution containing 6-(trans-4-propylcyclohexyl)-2-naphthol, 100.3 g (0.37 mol), in 200 ml of DMF was added dropwise to a slurry of SELECTFLUOR® reagent, 304.5 g (0.86 mol) in 250 ml of DMF while stirring under N$_2$. The temperature of the reaction mixture was maintained below 30° C. After the addition was completed, the reaction mixture was stirred at ambient temperature, and sampled periodically for analysis by gas chromatography. When the GC results showed no detectable starting material, the reaction was terminated. Toluene, 450 ml, and water, 375 ml, were added. The mixture was stirred and then transferred to a separatory funnel. The aqueous layer was withdrawn, and the organic layer was washed with 2×400 ml of water. An orange solid, 106.7 g (94% yield) was recovered after evaporation of the solvent from the organic phase. The product was characterized by GC and NMR analyses. This example shows that purification of the intermediate is not required.

Example 6

Synthesis of 1,1,2,2-tetrafluoro-6-(trans-4-propylcyclohexyl)-1,2-dihydronaphthalene 1,1-Difluoro-6-(trans-4-propylcyclohexyl)-1,2-dihydronaphthalene-2-one (47.9 g, 0.16 mol) was dissolved in toluene and charged to a TEFLON vessel. The reactor was purged with $N_2$, then sealed and heated to 60° C. When the temperature reached 60° C., DEOXO-FLUOR® reagent, 49.4 ml (0.27 mol), was added via syringe. The reaction mixture was stirred at 60–65° C. until GC analysis showed that the starting material had been consumed. The mixture was cooled to 10° C., and quenched by adding methanol then neutralized by adding 10% KOH. The mixture was transferred to a separatory funnel, and the aqueous layer was withdrawn. The organic layer was washed with 5% $NaHCO_3$ solution. The product, 48.5 g, was isolated as an oil after evaporation of the solvent and was analyzed by GC and NMR.

Example 7

Synthesis of 1,2-difluoro-6-(trans-4-propylcyclohexyl)naphthalene

A mixture of 1,1,2,2-tetrafluoro-6-(trans-4-propylcyclohexyl)-1,2-dihydronaphthalene and 1,1,2,4-tetrafluoro-6-(trans-4-propylcyclohexyl)-1,2-dihydronaphthalene, 10.0 g (30.6 mmol) in THF was stirred with zinc dust (10 g, 153 mmol) and aqueous 30% $NH_4OH$ at ambient temperature. After 27 h, GC analysis showed that the mixture contained <1% of the starting material. The mixture was filtered, and the zinc was washed with hexanes. The filtrate was transferred to a separatory funnel, the phases were separated, and the solvent was evaporated from the organic phase. The weight of product recovered was 8.6 g. GC analysis of the product showed that it contained 0.9% 1,1,2,2-tetrafluoro-6-(trans-4-propylcyclohexyl)-1,2-dihydronaphthalene, 13.4% 1,2,4-trifluoro-6-(trans-4-propylcyclohexyl)naphthalene, and 82% 1,2-difluoro-6-(trans-4-propylcyclohexyl)naphthalene. This example shows that when ammonia is not buffered to reduce the pH, more by-products are formed compared to the reaction in which buffered ammonia is used (Example 8).

Example 8

Synthesis of 1,2-difluor-6-(trans-4-propylcyclohexyl)naphthalene Using Buffered Ammonia A mixture of 1,1,2,2-tetrafluoro-6-(trans-4-propylcyclohexyl)-1,2-dihydronaphthalene and 1,1,2,4-tetrafluoro-6-(trans-4-propylcyclohexyl)-1,2-dihydronaphthalene, 25.6 g (78.4 mmol) in THF was stirred at ambient temperature with zinc dust (25.0 g, 382 mmol) and a solution containing ammonium chloride dissolved in aqueous 30% $NH_4OH$. The reaction was terminated after 48 h. The mixture was filtered, and the zinc was washed with hexanes. The filtrate was transferred to a separatory funnel, the phases were separated, and the solvent was evaporated from the organic phase. The weight of product recovered was 21.9 g. GC analysis of the product showed that it contained 0.2% 1,1,2,2-tetrafluoro-6-(trans-4-propylcyclohexyl)-1,2-dihydronaphthalene, 2.1% 1,2,4-trifluoro-6-(trans-4-propylcyclohexyl)naphthalene, and 93.1% 1,2-difluoro-6-(trans-4-propylcyclohexyl)naphthalene.

Example 9

Synthesis of 1,2-difluoro-6-(trans-4-propylcyclohexyl)naphthalene Using a Cu—Zn Catalyst 1,1,2,2-Tetrafluoro-6-(trans-4-propylcyclohexyl)-1,2-dihydronaphthalene, 10.0 g (30.6 mmol) in THF was stirred at ambient temperature with zinc dust (10 g, 153 mmol), copper powder (5.0 g, 79 mmol), and a solution containing ammonium chloride dissolved in aqueous 30% $NH_4OH$. The copper powder was prepared by reduction of copper sulfate pentahydrate with zinc. After 24 h, the reaction was terminated. The mixture was filtered, and the copper-zinc was washed with hexanes. The filtrate was transferred to a separatory funnel, the phases were separated, and the solvent was evaporated from the organic phase. The weight of product recovered was 8.2 g. GC analysis of the product showed that it contained 0.1% 1,1,2,2-tetrafluoro-6-(trans-4-propylcyclohexyl)-1,2-dihydronaphthalene, 1.7% 1,2,4-trifluoro-6-(trans-4-propylcyclohexyl)-naphthalene, and 94% 1,2-difluoro-6-(trans-4-propylcyclohexyl)naphthalene.

Example 10

Synthesis of 1,2-difluoronaphthalene from 2-hydroxynaphthalene (a) Formation of 1,1-difluoro-1H-naphthalene-2-one A suspension of 2-hydroxynaphthalene (5.0 g, 34.72 mmol) in DMF (50 ml) under $N_2$ was treated with SELECT-FLUOR® reagent (24.58 g, 69.44 mmol) in eight equal portions at 15 min intervals. The mixture was stirred for a further 1 h, diluted with 50 ml of ethyl acetate (EtOAc), washed with water (2×25 ml), dried ($MgSO_4$), filtered, and evaporated in vacuo. Purification by flash chromatography on silica gel (1:9 ethyl acetate/hexanes) furnished the product (6.12 g, 98% yield). MS: m/e 180 ($M^+$)

(b) Formation of 1,1,2,2-tetrafluoro-1,2-dihydronaphthalene

To a solution of 1,1-difluoro-1H-naphthalene-2-one (6.12 g, 34 mmol) in toluene (5 ml) under $N_2$ in a TEFLON tube was added the DEOXO-FLUOR® reagent (13.15 g, 10.9 ml, 59.5 mmol) and $BF_3.Et_2O$ (0.44 ml). The mixture was heated at 60° C. for 3 h. On cooling to 0° C., the solution was treated with MeOH (0.5 ml) and saturated $NaHCO_3$ (100 ml). After $CO_2$ evolution ceased, the solution was diluted with 20 ml toluene and the organic layer was separated, dried ($MgSO_4$), filtered, and evaporated in vacuo. The residue was purified by chromatography on silica gel (hexanes as solvent) to obtain the pure product (5.84 g, 85% yield as a 90/10 mixture of the title product and the 1,1,2,4-tetrafluoro isomer). MS: m/e 202 ($M^+$).

(c) Formation of 1,2-difluoronaphthalene

A solution of the tetrafluoro naphthalene, 1,1,2,2-tetrafluoro-1,2-dihydronaphthalene (5.25 g, 25.66 mmol) in THF (15 ml) was treated with 30% aqueous $NH_4OH$ (30 ml) and zinc (8.45 g, 130 mmol) (powder) and stirred under $N_2$ for 4 hours at RT. The reaction was monitored by GC/MS for disappearance of the starting material and found to be complete. The solution was filtered, extracted with hexane (30 ml), and filtered through a short silica column (20 g). The hexane solution was evaporated in vacuo to afford an oil. This crystallized on cooling to room temperature to afford 3.99 g (95% yield) of product. MS: m/e 164 ($M^+$).

Example 11

Synthesis of 1,2-difluoronaphthalene from 6-bromo-2-hydroxynaphthalene (a) Formation of 6-bromo-1,1-difluoro-1H-naphthalene-2-one A suspension of 6-bromo-2-hydroxynaphthalene (5.0 g, 22.42 mmol) in DMF (25 ml) under $N_2$ was treated with SELECTFLUOR® reagent (15.87 g, 44.84 mmol) in eight equal portions at 15 min intervals. The mixture was stirred for a further 1 h, diluted with EtOAc (50 ml), washed with water (2×25 ml), dried ($MgSO_4$), filtered, and evaporated in vacuo. Purification by flash chromatography on silica gel (1:9 ethyl acetate/hexanes) furnished the product (5.51 g, 95% yield). MS: m/e 259 ($M^+$).

(b) Formation of 6-bromo-1,1,2,2-tetrafluoro-1,2-dihydronaphthalene

To a solution of 6-bromo-1,1-difluoro-1H-naphthalene-2-one (5.51 g, 21.27 mmol) in toluene (5 ml) under $N_2$ in a TEFLON tube was added the DEOXO-FLUOR® reagent (8.42 g, 7.01 ml, 38.11 mmol) and $BF_3 \cdot Et_2O$ (0.282 ml, 2.24 mmol). The mixture was heated at 60° C. for 3 h. On cooling to 0° C., the solution was treated with MeOH (0.5 ml) and saturated $NaHCO_3$ (100 ml). After $CO_2$ evolution ceased, the solution was diluted with 20 ml toluene, and the organic layer was separated, dried ($MgSO_4$), filtered, and evaporated in vacuo. The residue was purified by chromatography on silica gel (hexanes as solvent) to obtain the pure product (4.78 g, 80% yield as a 85/15 mixture of the title product and the 1,1,2,4-tetrafluoro isomer). MS: m/e 281 ($M^+$).

(c) Formation of 1,2-difluoronaphthalene

A solution of the tetrafluoro naphthalene, 6-bromo-1,1,2,2-tetrafluoro-1,2-dihydronaphthalene (4.74 g, 16.80 mmol) in THF (15 ml) was treated with 30% aqueous $NH_4OH$ (30 ml) and zinc (8.45 g, 130 mmol) and stirred under $N_2$ for 24 hours at RT. The reaction was monitored by GC/MS for disappearance of the starting material and found to be complete. The solution was filtered, extracted with hexane (30 ml), and filtered through a short silica column (20 g). The hexane solution was evaporated in vacuo to afford an oil. This crystallized on cooling to room temperature to afford 2.62 g (95% yield) of product.

Example 12

Synthesis of 9,10-difluoro phenanthrene from 9-phenanthrol (a) Formation of 10,10-difluoro-10-H-phenanthrene-9-one A suspension of 9-phenanthrol (2.0 g, 10.31 mmol) in DMF (20 ml) under $N_2$ was treated with SELECTFLUOR® reagent (7.30 g, 20.62 mmol) in eight equal portions at 15 min intervals. The mixture was stirred for a further 1 h, diluted with EtOAc (50 ml), washed with water (2×25 ml), dried ($MgSO_4$), filtered, and evaporated in vacuo. Purification by flash chromatography on silica gel (1:9 ethyl acetate/hexanes) furnished the product (2.13 g, 90% yield). MS: m/e 230 ($M^+$).

(b) Formation of 9,9,10,10-tetrafluoro-9,10-dihydrophenanthrene

To a solution of 10,10-difluoro-10H-phenanthrene-9-one (2.13 g, 9.28 mmol) in toluene (5 ml) under $N_2$ in a TEFLON tube was added the DEOXO-FLUOR® reagent (3.87 g, 3.2 ml, 17.50 mmol) and $BF_3Et_2O$ (0.126 ml, 1.0 mmol). The mixture was heated at 60° C. for 3 h. On cooling to 0° C., the solution was treated with MeOH (0.5 ml) and saturated $NaHCO_3$ (100 ml). After $CO_2$ evolution ceased, the solution was diluted with 20 ml toluene and the organic layer was separated, dried ($MgSO_4$), filtered, and evaporated in vacuo. The residue was purified by chromatography on silica gel (hexanes as solvent) to obtain the pure product (1.96 g 84% yield). MS: m/e 252 ($M^+$).

(c) Formation of 9,10-difluorophenanthrene

A solution of the 9,9,10,10-tetrafluoro-9,10-dihydrophenanthrene (1.96 g, 7.75 mmol) in THF (15 ml) was treated with 30% aqueous $NH_4OH$ (30 ml) and zinc (2.52 g, 38.75 mmol) and stirred under $N_2$ for 24 hours at room temperature. The reaction was monitored by GC/MS for disappearance of the starting material and found to be complete. The solution was filtered, extracted with hexane (30 ml), and filtered through a short silica column (20 g). The hexane solution was evaporated in vacuo to afford an oil. This crystallized on cooling to room temperature to afford 1.58 g (95% yield) of product.

Example 13

Synthesis of 6-bromo-1,1-difluoro-1H-naphthalene-2-one

A solution containing 101.5 g (0.45 mol) of 6-bromo-2-naphthol in 265 ml of DMF was added dropwise to a slurry of 350 g (0.99 mol) of SELECTFLUOR® fluorinating reagent, in 220 ml of DMF, while stirring under $N_2$. The temperature of the reaction mixture was maintained below 30° C. After the addition was completed, the reaction mixture was stirred at ambient temperature, and sampled periodically for analysis by gas chromatography. When the GC results showed no detectable starting material, the reaction was terminated. Toluene (540 ml) was added,, and the mixture was stirred for 10 minutes then water (500 ml) was added. The mixture was stirred for an additional 10 minutes then was transferred to a separatory funnel. The aqueous layer was withdrawn, and the organic layer was washed with 2×500 ml of water. An orange solid (112.3 g, 96% yield) was recovered after evaporation of the solvent from the organic phase and drying under vacuum.

Example 14

Synthesis of 6-bromo-1,1,2,2-tetrafluoro-1,2-dihydronaphthalene

A solution of 6-bromo-1,1-difluoro-1H-naphthalene-2-one (20.3 g, 78.4 mmol) in toluene was charged to a TEFLON vessel. The reactor was purged with $N_2$, then sealed and heated to 60° C. When the temperature reached 60° C., 24.1 ml (130.7 mmol) of DEOXO-FLUOR® fluorinating reagent was added via syringe. The reaction mixture was stirred at 60–65° C. until GC analysis showed that the starting material had been consumed. The mixture was cooled to 10° C., and quenched by adding methanol then neutralized by adding 10% KOH. The mixture was transferred to a separatory funnel, and the aqueous layer was withdrawn. The organic layer was washed twice with water. The product was isolated as an oil after evaporation of the solvent.

Example 15

Synthesis of 6-bromo-1,1-difluoro-1H-naphthalene-2-one

Under nitrogen protection a solution of 670.0 g (3.0 mol) of 6-bromo-2-naphthol in 1800 ml of DMF was added slowly to a slurry of 2.35 kg (6.63 mol) of SELECT-FLUOR® reagent and 1400 ml of DMF. The temperature was kept between 8 and 14° C. After the addition was complete, the mixture was stirred at a temperature below 21° C. until no starting material was identified by GC. MTBE (3600 ml) was added, the mixture was stirred for 10 minutes, then water (3000 ml) was added, and the mixture was stirred for another 10 minutes. The aqueous phase was separated, and the organic phase was washed twice with water, and then dried over $MgSO_4$. The $MgSO_4$ was filtered off, and the solvent was removed under vacuum. A yellow solid (674.2 g, 2.6 mol) remained. Additional product was recovered by adding NaCl to the aqueous phase and extracting three times with MTBE. The combined organic layer was washed three times with water and dried with $MgSO_4$. The $MgSO_4$ was filtered off, and the solvent was removed under vacuum leaving a yellow solid (79.7 g, 0.3 mol). This material was added to the previously isolated product. The combined yield was 97%.

Example 16

Synthesis of 6-bromo-1,1,2,2-tetrafluoro-1,2-dihydronaphthalene

A 300 ml stainless steel autoclave was charged with 110.2 g (0.425 mol) of 6-bromo-1,1-difluoro-1H-naphthalene-2-one. Anhydrous HF (8.5 g, 0.43 mol) and 69.1 g (0.639 mol) of $SF_4$ were condensed at about −40° C. into the reactor. The vessel was allowed to warm up, and the reaction mixture was stirred for about 3 hours. The temperature was kept below about 25° C. by placing the reactor into a water bath. When the reaction was complete, the reactor was vented and then evacuated to remove the volatiles, leaving the product in the reactor. The product was neutralized with aqueous $Na_2CO_3$, and the reactor was rinsed with aqueous $NaHCO_3$. The phases were separated, and the aqueous layer was extracted 3 times with hexanes. The combined organic layer was washed twice with brine and stored over $MgSO_4$ and silica gel. The $MgSO_4$ and silica gel were filtered off, and the solvent was removed under vacuum. A dark red liquid (117.3 g, 0.42 mol, 98% yield) remained.

Example 17

Synthesis of 6-bromo-1,2-difluoronaphthalene

Zinc (2.439 g, 36.6 mmol) was added to a stirred mixture of 5.01 g (17.8 mmol) of 6-bromo-1,1,2,2-tetrafluoro-1,2-dihydronaphthalene, 11 ml of THF, and 22 ml of $NH_4OH$ that was cooled in an ice bath. The mixture was allowed to warm slowly to room temperature. After 4½ hours reaction time, the zinc was removed by filtration. The phases were separated, and the aqueous layer was extracted three times with hexanes. The combined organic phase was washed twice with brine and dried over $MgSO_4$. The $MgSO_4$ was filtered off, and the solvent removed under vacuum. Crude 6-bromo-1,2-difluoronaphthalene (4 g) containing 15% impurities (estimated) remained. The estimated yield of the crude 6-bromo-1,2-difluoronaphthalene was 91%. Brown needles (2.0 g, 8.3 mmol, 46% yield) were recovered after recrystallization from hexanes.

Example 18

Synthesis of 6-bromo-1,2-difluoronaphthalene

Zinc (7.06 g, 108 mmol) was added to a stirred mixture of 20.0 g (71.2 mmol) of 6-bromo-1,1,2,2-tetrafluoro-1,2-dihydronaphthalene, 44 ml of THF, 20.1 g of $NH_4Cl$ and 90 ml of $NH_4OH$ that was cooled in an ice bath. The mixture was allowed to warm slowly to room temperature. After 5 hours reaction time, the zinc was removed by filtration. The phases were separated, and the aqueous layer was extracted three times with hexanes. The combined organic phase was washed twice with brine and dried over $MgSO_4$. The $MgSO_4$ was filtered off, and the solvent was removed under vacuum. Crude 6-bromo-1,2-difluoronaphthalene (16.4 g) containing 15% impurities (estimated) remained. The estimated yield of the crude 6-bromo-1,2-difluoronaphthalene was 85%. Recrystallization of the crude solid from methanol/water yielded light brown needles (13.6 g, 55.8 mmol, 77% yield).

Example 19

Synthesis of 6-bromo-1,2-difluoronaphthalene

Zinc (7.18 g, 110 mmol) was added in two portions (4.74 g and 2.44 g) to a stirred mixture of 20.1 g (71.4 mmol) of 6-bromo-1,1,2,2-tetrafluoro-1,2-dihydronaphthalene, 45 ml of THF, 20.1 g of $NH_4Cl$, and 90 ml of $NH_4OH$ that was cooled in an ice bath. The mixture was allowed to warm slowly to room temperature. After 5 hours reaction time, the zinc was removed by filtration. The phases were separated, and the aqueous layer was extracted three times with hexanes. The combined organic phase was washed twice with brine and dried over $MgSO_4$. The $MgSO_4$ was filtered off, and the solvent was removed under vacuum. Crude 6-bromo-1,2-difluoronaphthalene (16.7 g) containing 15% impurities (estimated) remained. The estimated yield of the crude 6-bromo-1,2-difluoronaphthalene was 86%. The crude yellow solid was sublimed at 70–80° C. Off-white needles (14.5 g, 59.5 mmol, 83% yield) were collected.

Example 20

Synthesis of 6-bromo-1,2-difluoronaphthalene

A cold solution (0° C. bath temperature) of 240.1 g of $NH_4Cl$ in 1,080 ml of $NH_4OH$ was added to a stirred mixture of 82.7 g (1.3 mol) of zinc, 236.2 g (0.8 mol) of 6-bromo-1,1,2,2-tetrafluoro-1,2-dihydronaphthalene, and 540 ml of THF that was cooled to 3° C. in an ice bath. The mixture was allowed to warm slowly to room temperature. After 7 hours reaction time, the zinc was removed by filtration. The phases were separated, and the aqueous layer was extracted three times with hexanes. The combined organic phase was washed twice with brine and stirred over $MgSO_4$ and activated carbon for 3 h. The mixture was stored for 15 h. The $MgSO_4$ and carbon were filtered off, and the solvent was removed under vacuum. Crude 6-bromo-1,2-difluoronaphthalene (194.8 g) remained. The solid was dissolved in hexanes, and silica gel was added to the solution. The mixture was stirred for 10 minutes then was allowed to stand for 15 h. Additional silica gel was added to the mixture. A part of the product crystallized so hexane was added, and the mixture was stirred for 2.5 h. The silica gel was filtered off, and the solvent was removed under vacuum. A beige solid (192.9 g) remained. The solid was purified by heating under vacuum to 70° C. The final product was a light beige solid (174.9 g, 0.7 mol, 85%).

Example 21

Synthesis of 6-bromo-1,2-difluoronaphthalene

Zinc (0.89 g, 14 mmol) was added to a stirred mixture of 2.4 g (8.7 mmol) of 6-bromo-1,1,2,2-tetrafluoro-1,2- dihydronaphthalene, 4 ml of water, 6 ml of THF, and 7.6 g of tetramethylammonium hydroxide pentahydrate that was cooled in an ice bath. The mixture was allowed to warm to room temperature. After 2 hours, the zinc was filtered, and the phases were separated. The aqueous layer was extracted three times with hexanes. The combined organic phase was washed three times with brine, stirred over $MgSO_4$ and activated carbon for 3 hours, and then stored for 15 hours. The $MgSO_4$ and carbon were filtered off, and the solvent was removed under vacuum. A colorless solid (1.9 g, 7.7 mmol, 89%) remained.

Example 22

Synthesis of 6-chloro-1,2-difluoronaphthalene

A cold solution of 2.3 g of $NH_4Cl$ in 10 ml of $NH_4OH$ was added to a stirred mixture of 2.00 g (8.45 mmol) of 6-chloro-1,1,2,2-tetrafluoro-1,2-dihydronaphthalene, 5 ml of THF, and 0.84 g (13 mmol) of zinc that was cooled in an ice bath. The mixture was allowed to warm slowly to room temperature. After 22 h, 0.31 g (4.8 mmol) of additional zinc and 3 ml of $NH_4OH$ were added. After 24 h reaction time, the zinc was removed by filtration. The phases were separated, and the aqueous layer was extracted three times with hexanes. The combined organic phase was washed twice with brine, dried over $MgSO_4$ and decolorized with activated carbon. The $MgSO_4$ and carbon were filtered off, and the solvent was removed under vacuum. A colorless solid (1.6 g, 7.8 mmol, 92% yield) remained.

While the invention has been described in detail and with reference to specific examples thereof, it will be apparent to one skilled in the art that various changes and modifications can be made therein without departing from the spirit and scope thereof.

What is claimed is:

1. A method for making an aromatic compound having two vicinal fluorine atoms, wherein said aromatic compound is selected from the group consisting of monocyclic aromatic ring, bicyclic separate aromatic rings, bicyclic fused aromatic rings tricyclic separate aromatic rings, tricyclic fused aromatic rings and mixtures thereof, comprising:

mixing a tetrafluoro derivative of an aromatic compound with a reducing agent in a presence of a base for a time needed to form an aromatic compound containing two vicinal fluorine atoms, said tetrafluoro aromatic compound having two fluorine atoms on each of two adjacent carbons on the ring.

2. The method of claim 1, wherein the tetrafluoro derivative of a halogen substituted aromatic compound is mixed with an organic solvent.

3. The method of claim 2, wherein said organic solvent is a member selected from the group consisting of tetrahydrofuran, methyl tert-butyl ether, acetonitrile, ethanol, and dimethylformamide.

4. The method of claim 1, wherein the base is ammonium hydroxide, hydroxylamine, hydrazine, or a substituted ammonium hydroxide.

5. The method of claim 4, wherein the substituted ammonium hydroxide is a member selected from the group consisting of tetramethylammonium hydroxide, ethyl ammonium hydroxide, and benzyltrimethyl ammonium hydroxide.

6. The method of claim 5, wherein the substituted ammonium hydroxide is tetramethylammonium hydroxide.

7. The method of claim 4, wherein the base is buffered to maintain a pH below 14.

8. The method of claim 1, wherein the reducing agent is present at −25 to 90° C.

9. The method of claim 1, wherein the aromatic compound having two vicinal fluorine atoms is a vicinal difluoro halogenated aromatic compound.

10. The method of claim 1, wherein a ring of the aromatic compound contains a heteroatom selected from the group consisting of oxygen, nitrogen, sulfur and mixtures thereof.

11. The method of claim 1, wherein a ring of the aromatic compound contains a substitution selected from the group consisting of halogen atom, a $C_1$ to $C_{20}$ alkyl, a $C_5$–$C_{10}$ cycloalkyl, a $C_6$ to $C_{12}$ aryl, an amino, a nitro, a $C_1$ to $C_{10}$ alkyl ether or thioether, a $C_1$ to $C_{10}$ alkyl ester, a $CF_3$, a $R'SO_2O$,

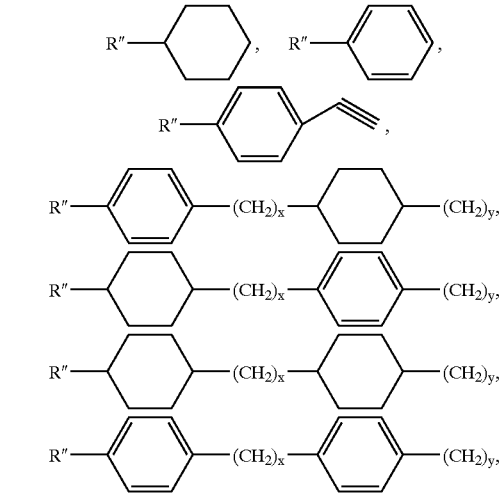

where R' is $CF_3$, a $C_1$ to $C_{20}$ alkyl, a substituted or unsubstituted $C_5$ to $C_{10}$ cycloalkyl, or a substituted or unsubstituted $C_6$ to $C_{12}$ aryl, in which the substitution on the cycloalkyl or aryl can be a $C_1$ to $C_{20}$ alkyl or a $C_5$ to $C_8$ cycloalkyl; R" is a $C_1$–$C_{10}$ saturated or unsaturated alkyl; x is an integer from 0 to 10, and y is an integer from 0 to 10, and mixtures thereof.

* * * * *